United States Patent [19]

Athayde et al.

[11] Patent Number: 5,257,987
[45] Date of Patent: Nov. 2, 1993

[54] CONTROLLED RELEASE OSMOTIC INFUSION SYSTEM

[75] Inventors: Amulya L. Athayde, Mountain View; Rolf A. Faste, Stanford, both of Calif.

[73] Assignee: PharMetrix Corporation, Menlo Park, Calif.

[21] Appl. No.: 526,120

[22] Filed: May 21, 1990

[51] Int. Cl.⁵ .............................. A61K 9/22
[52] U.S. Cl. .................. 604/892.1; 604/131; 604/87; 128/DIG. 2
[58] Field of Search .............. 604/892.1, 131, 141, 604/148, 151, 86, 87; 128/DIG. 12

[56] References Cited

U.S. PATENT DOCUMENTS

| | | |
|---|---|---|
| 3,760,805 | 9/1973 | Higuchi . |
| 4,034,756 | 7/1977 | Higuchi et al. . |
| 4,191,181 | 3/1980 | Franetzki et al. . |
| 4,193,398 | 3/1980 | Refson . |
| 4,201,207 | 5/1980 | Buckles et al. . |
| 4,398,908 | 8/1983 | Siposs . |
| 4,474,575 | 10/1984 | Eckenhoff et al. . |
| 4,525,164 | 6/1985 | Loeb et al. . |
| 4,552,561 | 11/1985 | Eckenhoff et al. ......... 604/131 |
| 4,596,575 | 6/1986 | Rosenberg et al. . |
| 4,608,043 | 8/1986 | Larkin ......... 604/87 |
| 4,744,786 | 5/1988 | Hooven ......... 128/DIG. 12 |
| 4,783,413 | 11/1988 | Suter ......... 604/892.1 |
| 4,838,862 | 6/1989 | Baker et al. ......... 604/892.1 |
| 4,898,582 | 2/1990 | Faste ......... 604/892.1 |
| 4,902,278 | 2/1990 | Maget et al. ......... 128/DIG. 12 |
| 4,969,873 | 11/1990 | Steinbach et al. ......... 128/DIG. 12 |

OTHER PUBLICATIONS

M. J. Sefton et al, "Controlled Release Micropump For Insulin Administration", Ann. Biomed. Eng., vol. 7, pp. 329-343, (1979).

J. Bottino et al., "Continuous Intravenous Arabinosyl Infusions Delivered by a New Portable Infusion System", Cancer, vol. 43, pp. 2197-2201, (1970).

S. Rose et al., "A Continuous Long-Term Injector", Austral. J. Biol., vol. 33, pp. 415-420, (1955).

Product Brochure, Pump Model AS*2F, Auto-Syringe, Inc. Hookset, New Hampshire.

Product Brochure, Pump Model AS*3B, Auto-Syringe, Inc. Hookset, New Hampshire.

Product Brochure, Pump Model AS*5B, Auto-Syringe, Inc. Hookset, New Hampshire.

Product Brochure, Pump Model AS*6C, Auto-Syringe, Inc. Hookset, New Hampshire.

Product Brochure, Pump Model ML6, Cormed, Inc., Middleport, N.Y.

*Primary Examiner*—C. Fred Rosenbaum
*Assistant Examiner*—Mark O. Polutta
*Attorney, Agent, or Firm*—Townsend and Townsend Khourie and Crew

[57] ABSTRACT

A portable osmotic infusion device assembly, having two pouches in pressure transmitting relationship, the first containing infusate and the second, a driving fluid. The driving fluid is created and pressurized by activation of an osmotic pump, and the rate of infusion is controlled by a rate-controlling means. The infusate pouch is manufactured separately and can be stored apart from the rest of the system.

24 Claims, 5 Drawing Sheets

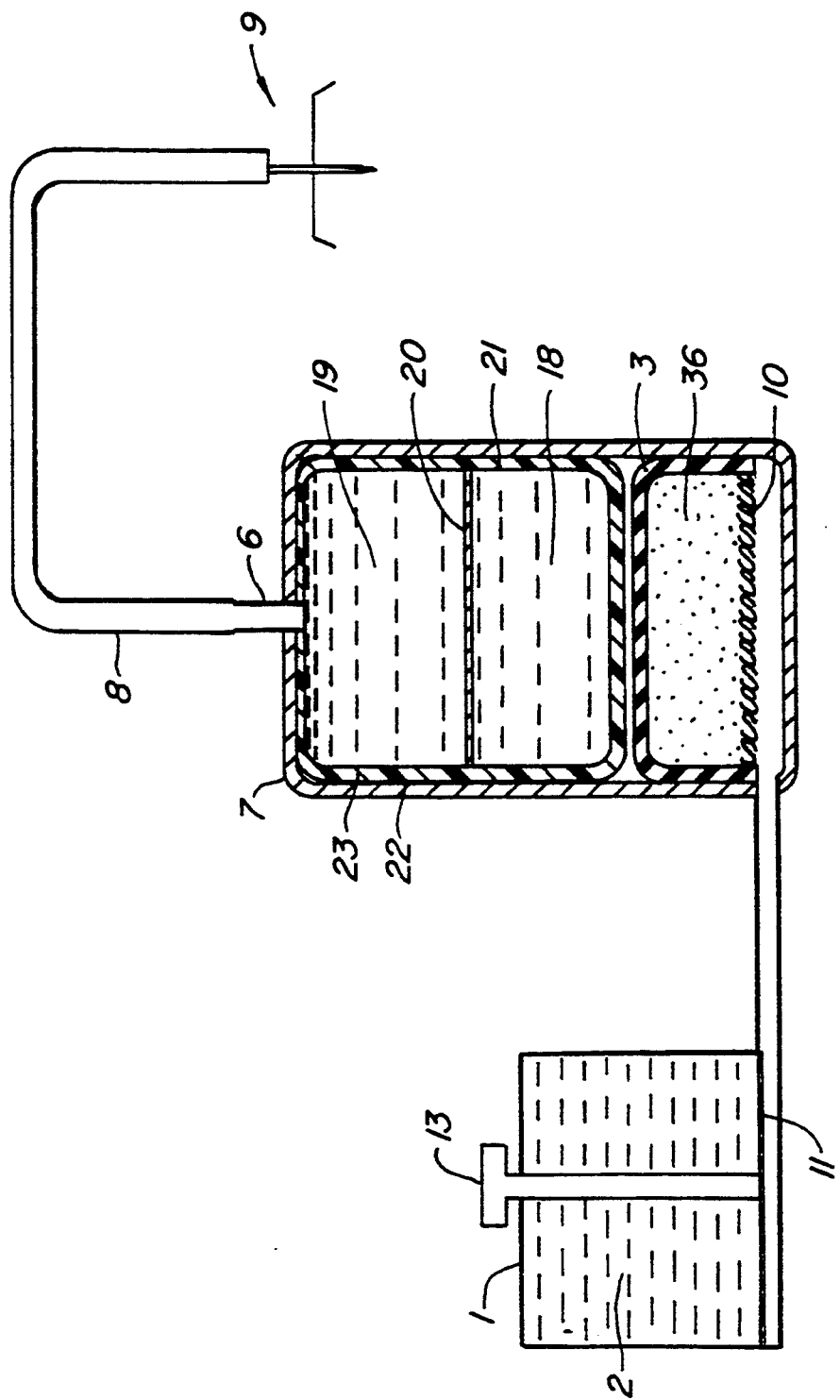

CONTROLLED RELEASE OSMOTIC INFUSION SYSTEM

FIELD OF THE INVENTION

This invention relates to controlled release osmotic infusion devices, and particularly to small portable body-mounted devices capable of delivering liquids such as drugs or other pharmaceutical agents for prolonged periods, where the liquid is contained in a flexible pouch within the device.

BACKGROUND OF THE INVENTION

Many kinds of parenteral drug therapy require continuous drug delivery in preference to single or multiple drug injections. Benefits that accrue from continuous therapy may include, for instance, reduction of toxic or other side effects associated with sharp pulses of drug, significant improvement in the effectiveness of the therapy through the use of smaller amounts of drug, and increased patient comfort. The traditional manner of administering sustained parenteral treatments is via intravenous drip. Intravenous drip treatment is commonplace in a hospital environment, but this treatment mode obviously imposes severe restrictions on the activity of the recipient. As a result, considerable research over the last few years has been devoted to the development of small portable infusion pumps. A range of devices has appeared, including those with electric or clockwork motors that drive syringe or peristaltic pumps, and others powered by the elastic tension of an inflated balloon, or the vapor pressure of a volatile propellant. Literature incorporated herein by reference describing such pumps are *Controlled Release Micropump for Insulin Administration*, (M. V. Sefton et al., Ann. Biomed. Eng., Vol. 7, pp. 329-343, 1979), *Continuous Intravenous Arabinosyl Cytosine Infusions Delivered by a New Portable Infusion System*, (J. Bottino et al., Cancer, Vol. 43, pp. 2197-2201, 1979), or product brochures from Auto-Syringe, Inc., Hooksett, New Hampshire and Cormed, Inc., Medina, New York. These devices are typically strapped onto the wearer, or carried on a belt or in a harness. Also, most are designed to deliver relatively large quantities of fluid and do not effectively dispense small volumes of the order of a few milliliters or less.

An alternative approach that has been exploited to a limited extent is to drive the infusion device osmotically, using a Rose-Nelson pump, activated by imbibition of water or other driving fluid. The principle of the osmotic pump was originally conceived by Rose and Nelson in the 1950's (S. Rose and J. F. Nelson, "A Continuous Long-Term Injector," *Austral. J. Exp. Biol.* 33, pp. 415-420 (1955)). A Rose-Nelson pump consists of three chambers: a salt chamber containing excess solid salt, a drug chamber, and a water chamber. The salt and water compartments are separated by a rigid membrane permeable to water but impermeable to ionized and hydrated salt ions; the salt and drug chambers are separated by a rubber diaphragm. In operation, water is imbibed osmotically into the salt chamber, causing the rubber diaphragm to expand into the drug chamber and forcing the drug out through the delivery orifice. Depending on the salt used, the osmotic pressure developed by this type of pump is usually between 50 and 200 atmospheres. The pressure required to pump the drug from the device is small in comparison, and hence the drug delivery rate remains constant as long as some excess undissolved salt remains in the salt chamber. In comparison with mechanically-driven devices, Rose-Nelson pumps are small, reliable, and simple and inexpensive to manufacture. U.S. Pat. No. 3,604,417 discloses a modification of the Rose-Nelson pump in which a movable piston replaces the elastic diaphragm separating the drug and salt chamber, and both the drug and salt are loaded into the pump as solutions. U.S. Pat. No. 4,474,048 discloses another modification of the Rose-Nelson principal employing an impermeable elastic wall, and a movable end wall that can be screwed in to deliver a pulse dose of the contained drug at any time during the operation of the pump. U.S. Pat. No. 4,474,575 is a variant of U.S. Pat. No. 4,474,048 in which the flow rate of the dispensed agent can be varied blistering the area of semipermeable membrane exposed to the water chamber. U.S. Pat. No. 4,552,651 discloses a pump assembly with a small osmotic pump that can be filled in advance of use with the active agent to be dispensed. The action of this pump is initiated by filling the lower chamber of the housing with a hydrogel. Once the pump is in action, an optional mechanism for delivering pulse doses can be employed. All these osmotic pumps are self-driven and begin to operate as soon as all of the several chambers are filled with their fluid contents and liquid is imbibed across the semipermeable membrane into the salt chamber. The mechanisms of activation of these pumps, however, are quite impractical, because they require that the user fill one or more of the pump chambers with solution. This type of activation means is far too complicated for pumps that are meant to be used by patients or patient family members in a home care environment.

U.S. Pat. No. 4,838,862, commonly owned with the present application and incorporated herein by reference in its entirety, describes a portable osmotic infusion pump that can be filled with the agent to be dispensed, the osmotic salt and the imbibing fluid, and then stored as a complete assembly, ready for activation and use without need for addition of other components. U.S. Pat. No. 4,898,582, also commonly owned with the present application and incorporated herein by reference in its entirety, describes a portable osmotic pump that includes a housing with two side-by-side compartments, where one compartment contains the drug or agent to be infused and the osmotic salt chamber, and the second compartment contains the imbibing fluid for the pump. The latter two patents describe osmotic pumps that can be filled with all required fluids, including the drugs to be delivered, stored until needed, and then activated very rapidly and simply on demand. They are therefore excellent systems for use as disposable drug infusion devices.

Nevertheless, many limitations of these devices have not yet been addressed or resolved. One common limitation is that long-term storage of the devices presents problems associated with drug stability and integrity. Many substances such as drugs fare poorly when stored, especially when stored in solution. The drug, when stored in a delivery device for a period of time, may change or deteriorate chemically and pharmacologically, and may precipitate out of solution. The drug may also react chemically with other components of the system that diffuse from various parts of the assembly into the drug chamber. This aspect of production, sterilization, and storage of a drug-bearing device is not adequately addressed in available disposable infusion devices and is a problem that therefore limits their use. Another limitation of some of these devices is related to the fact that there is, commonly, only one barrier between the infusate and driving fluid, for example, a rubber diaphragm. This configuration creates potential safety problems for the user. Any tear or leak in the wall of the reservoir containing the infusate permits mixing of the infusate with the driving fluid, which will result in contamination of the infusate. Such contamination would be potentially harmful to the patient if it happened during use and went undetected, particularly if the driving fluid was contaminated by bacteria or other harmful substances. Clearly, it is possible to choose a driving fluid that would not be harmful to the patient if this accidental mixing were to occur, but the requirement of sterilization of the driving fluid, and preservation of the driving fluid's sterility during use, is yet another obstacle in the creation of a device that is simple and cost-effective to manufacture.

One means for resolving the problems of long-term infusate storage that is described in detail in this application is accomplished by containing the infusate in a removable flexible pouch within the device. In one embodiment of the invention, the pouch could be a part of the device that is filled with the infusate during manufacture, or later, for example by a pharmacist or other person, a short time before the device is used. There are many instances in the patent literature of infusion pupils where the liquid infusate is contained in a separate pouch within the device. U.S. Pat. No. 4,034,756 discloses a small osmotic pump for use in an aqueous environment, such as the gastrointestinal tract, in which the liquid infusate (e.g. a drug solution) is contained in a flexible bag within the device, and the osmotic fluid pressure is exerted directly on the flexible bag to effect infusate delivery. The flexible bag of this patent can be filled with the infusate during pump manufacture, or the bag can be filled with the infusate at a later time. This pump can be activated only by exposure to the aqueous environment, and is therefore limited generally to internal use for drug delivery. The activation means consists of the user swallowing the device or otherwise exposing the device to internal fluids, and rate control is solely a function of the permeability characteristics of the outer semipermeable layer.

U.S. Pat. No. 3,760,805 describes an osmotic dispenser comprised of a water porous housing confining a first flexible bag of relatively impervious material containing an active agent, and a second bag of controlled permeability to moisture containing an osmotic solution. The first and second bags are disposed within the housing such that water permeates from the external environment through the housing and migrates by osmosis into the solution contained in the second bag. The second bag increases in volume, thereby generating mechanical force on the first bag and ejecting the active agent out of the device. This pump, designed primarily for ingestion or implantation, depends upon permeation of water from the environment, e.g. the gastrointestinal tract, and therefore is unsuitable for subcutaneous infusion.

Other patents in the literature describe portable infusion pumps that contain the infusate in pouches within the device but that incorporate other motive means besides osmosis. U.S. Pat. No. 4,201,207 discloses an elastic bladder pump filled with liquid under pressure, which is powered by the elastic tension of the bladder. This device also includes a flow control element between the bladder and the catheter fitting to deliver the liquid infusate to the patient. U.S. Pat. No. 4,191,181 discloses a liquid infusion pump with a power supply such as a battery and a refillable flexible infusate reservoir. This pump can be activated on demand and has a flow control means that acts directly on the pumping mechanism, which is downstream from the infusate reservoir. U.S. Pat. No. 4,596,575 discloses an implantable liquid infusion pump that is particularly intended for the delivery of insulin. It contains two collapsible reservoirs in rigid housings, and also a mechanical pump that is regulated by an electronic unit control for management of pump activation and flow rate. One of the reservoirs contains the infusate; the space between the outer wall of this reservoir and its rigid housing is filled with the drive liquid. The second reservoir is filled with the drive liquid, and the space between the outer wall of this reservoir and its rigid housing is maintained at subambient pressure. The drive liquid is pumped from the second reservoir into the outer space of the first housing to exert pressure on the first reservoir and thus deliver the liquid infusate. The electronic control unit regulates two valves that restrict the flow rate of the drive liquid. The device is also provided with a separate refill system that may be used to refill the infusate reservoir.

Other patents in the literature describe portable infusion pumps that contain flexible pouches containing the infusate fluid that are removable from the device, or that can be loaded separately into the device after manufacture of the main pump assembly. U.S. Pat. No. 4,193,398, for example, discloses an extracorporeal osmotic pump in which the infusate liquid is contained in a flexible pouch that is located within a second pouch containing the osmotic fluid. This pump also contains an additional chamber filled with the driving fluid for the pump, for example water or a weak osmotic solution, and incorporates rate-control and activation means. U.S. Pat. No. 4,398,908 discloses an infusion pump driven by electromechanical power, in which insulin is stored in a flexible pouch that is removable and replaceable, as is the pumping mechanism described. This pump can be activated on demand and incorporates a rate-control mechanism. The pumping mechanism, which incorporates the activation and rate-control means, is downstream from the insulin reservoir, and therefore comes in direct contact with the insulin infusate. U.S. Pat. No. 4,525,164 discloses a motor-driven pump with a removable and replaceable arcuated reservoir, in which a piston applies pressure directly to a portion of the reservoir to propel the drug out of the device. This device incorporates a means for activating the pump motor and controlling the pumping rate.

Each of these references describes an infusion pump that incorporates a separately, loaded pouch or reservoir in a specific configuration, and usually with a specific motive force, yet all have problems that have inhibited their use. These problems include a high cost of manufacture, difficulties in sterilizing the drug chamber and contents, difficulties in maintaining sterility of the device, and problems with stability of the devices after prolonged storage. A particular problem with many of these devices is that the delivery rate of the infusate is controlled by directly regulating the flow of the infusate out of the device, for example, by a valve to control the flow rate. This configuration presents problems with sterilization of the device, due to the presence of small compartments and crevices in contact with the infusate that may be difficult for the sterilizing agent to reach. Another problem with flow regulation of the infusate fluid is that shear effects created, for example, by fluid passing through a valve, may lead to degradation of the molecules of drug in solution. Proteins or other large molecules, for example, are particularly susceptible to shear degradation. Moreover, reliable regulation of these very low flow rates is inherently difficult. As a result, there remains a need for a reliable disposable infusion pump that can be loaded with sterile liquid infusate, that can maintain sterility during prolonged storage, and that can be activated on demand to provide the required pattern of delivery of very low infusate flow rates.

The present invention describes an osmotic infusion pump assembly that incorporates an infusate pouch that can be manufactured, sterilized, and aseptically loaded with infusate and assembled into a sterile pump assembly, or sterilized separately from the other components of the assembly and then loaded into the pump assembly at the appropriate time. The pump is small, light, and convenient for patient use, and can be activated by the patient or the primary care giver immediately prior to the placement of the pump on the body. The infusate pouch of this invention is simple in design, and therefore would be straightforward to manufacture and sterilize. It can also be made of nonelastic materials and therefore can be constructed using materials that are relatively impervious to invasion by environmental agents such as oxygen, carbon dioxide, or substances that are derived from components of the device. The rate of delivery of the infusate from this pouch is controlled by the expansion of a second pressure-transmitting pouch. Pressure is obtained by filling the second pressure-transmitting pouch with a driving fluid at a controlled rate.

Presentation of sterile medication to the patient via infusion devices presents several unique problems in drug stability and sterility. Deposition of a drug solution into a cavity within an infusion device just prior to application requires presterilization of that cavity and delivery of a unit dose of sterile drug to the aforesaid cavity in an aseptic manner. Some methods of sterilization may be suited for some materials but totally unacceptable for other desired components. Many drugs and solutions may be rendered sterile by gamma radiation, but polypropylene components subjected to sterilizing doses of gamma radiation suffer severe radiation-induced degradation. Metals may be advantageously sterilized using steam, but many drugs cannot withstand the steam sterilization regime. The separation of the filling and sterilization of the infusate pouch from the manufacture and treatment of the remainder of the infusion device permits optimization of the sterilizing procedure. For example, the infusate pouch may be manufactured and sterilized under conditions most suited for the materials of pouch construction. Then, at a later date, the sterile pouches may be aseptically filled with unit doses of drug solution that have been presterilized by conventional means; or alternately, the solutions may be sterilized by sterile filtration at the point of filling and the pouches sealed. These sterile dose units may then be assembled into the remainder of the infusion device or stored and shipped separately. Since the contents of the infusate pouch do not come into direct contact with the other components of the pump, it is not essential that the remainder of the device be manufactured and maintained under sterile conditions.

Drugs that have limited lifetimes in solution may be stored in a dry or lyophilized form in a two-component embodiment of the infusate pouch. In this pouch, one compartment contains the drug and another contains solvent for the drug in a separate sealed part of the pouch. The seal between the two compartments is broken just prior to use, the contents are mixed in the pouch, the pouch loaded into the infusion device, and the device is activated and attached. In this way, the shelf-life of the drug is dependent solely upon the storage conditions of the drug-containing infusate pouch.

SUMMARY OF THE INVENTION

Objects of the invention

It is an object of the invention to provide a portable controlled release infusion device that can be stored, with or without the infusate, for prolonged periods without deterioration.

It is an object of the invention to provide a disposable, portable controlled release infusion device that can be stored, with or without the infusate, for prolonged periods without deterioration.

It is another object of the invention to provide a portable controlled release infusion device wherein each individual device can be used to deliver any of a variety of different liquids, including different drugs.

It is another object of the invention to provide a portable controlled release infusion device wherein the infusate is protected from contamination by other substances both during storage and in use.

It is another object of the invention to provide a portable controlled release infusion device that is inexpensive and straightforward to manufacture.

It is another object of the invention to provide a portable controlled release infusion device that can be easily sterilized and maintained in a sterile and contaminant-free state after prolonged storage.

It is another object of the invention to prepare a portable controlled release infusion device that can be stored sterile for a period of up to two years or longer without impairment of its infusate delivery function.

It is another object of the invention to provide a portable controlled release infusion device that can be activated quickly and simply on demand.

Other objects and advantages of the invention will be apparent to those of ordinary skill in the art from the description that follows.

BRIEF DESCRIPTION OF THE DRAWINGS

FIG. 5 is a diagram of an embodiment of the invention for which the infusate is contained in lyophilized form in a pouch with two compartments, with a seal separating the infusate from a liquid solvent.

DESCRIPTION OF THE INVENTION

Figure 1:
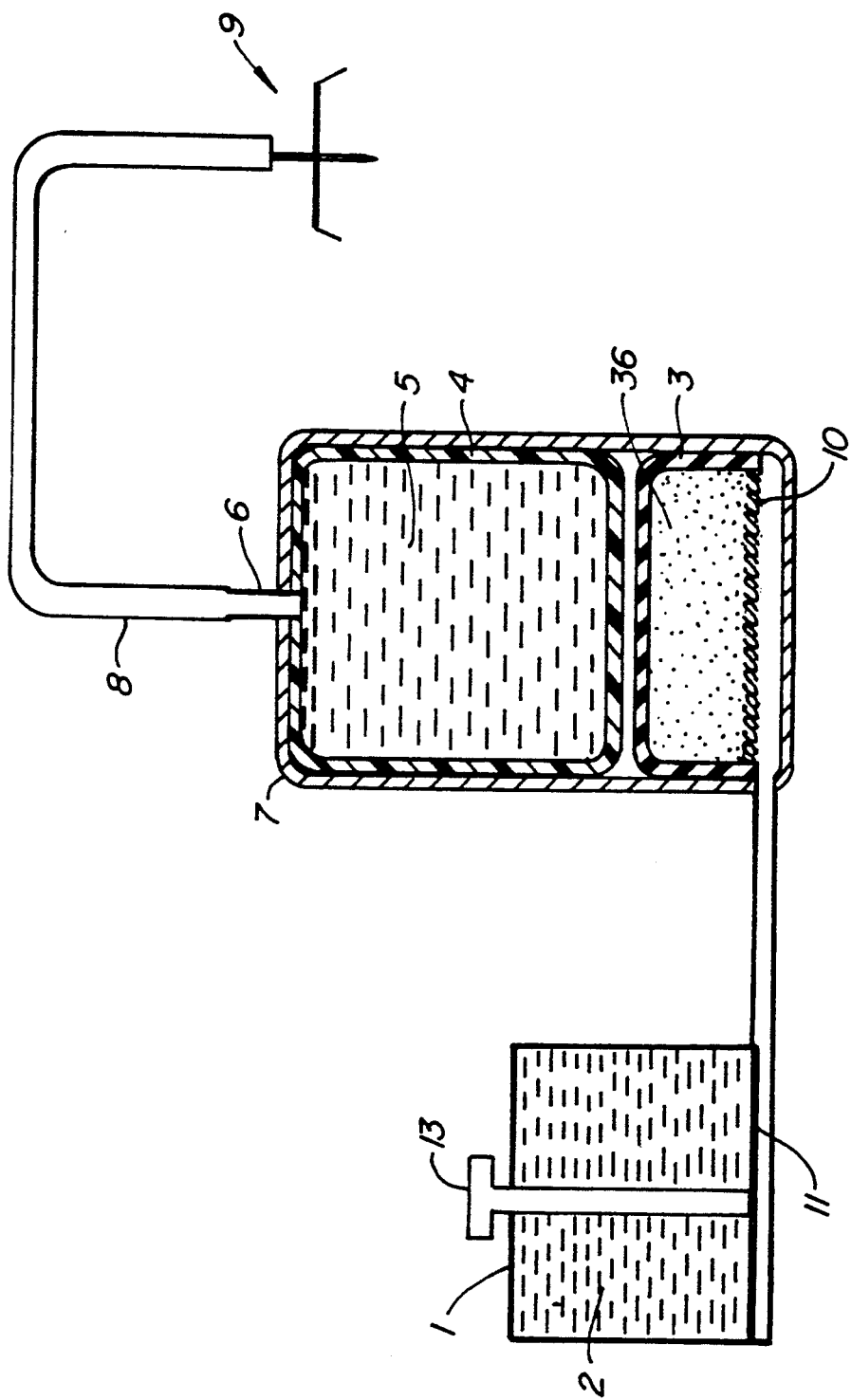
FIG. 1 is a diagram of the basic features of the invention, which is a Rose-Nelson osmotic pump with an elastic pouch for containment of the driving fluid, and a flexible pouch for containment of the infusate.

To achieve the foregoing objects, the present invention provides a portable controlled release infusion pump assembly. The assembly includes two chambers, where two containers (an elastic pouch and a flexible pouch) are held in the first chamber and a power source is contained in the second chamber. The first chamber is contained in a restraining outer housing that restricts movement of the two pouches. Preferably, the entire device is contained in a second unitary protective housing so as to protect the device from the environment. The protective housing can be made of metal or plastic, and would normally be made by any conventional mass-production technique. The dimensions of the housing will vary according to the volume of the chambers that are contained. The first chamber of the pump houses a first flexible pouch that is preferably sterilizable and under neutral pressure. This flexible pouch contains the infusate, preferably in liquid form. This first chamber also houses a second pouch, called the pressure-transmitting pouch, containing the driving fluid as it is created by the pressure-generating means. These pouches are positioned in the chamber with a minimal free volume between the pouches, and the pouches have a surface area by which pressure is transmitted from the pressure-transmitting pouch to the pouch containing the infusate. Preferably, these two pouches completely fill the chamber in which they are placed. The assembly also includes a second chamber that contains the power source as herein defined, which consists of a pressure-generating means, based on the principle of osmosis as in the Rose-Nelson pump; an activating means; and a means of controlling the pressure increase in the pressure-transmitting pouch, and thus the infusate flow rate out of the device. The pressure-generating means will cause the delivery of the driving fluid to the pressure-transmitting pouch, which will then exert pressure on the infusate delivery pouch. Activation of the device by the user will cause delivery of the driving fluid to the pressure(transmitting pouch. The rate at which the driving fluid is created in the pressure transmitting pouch will be controlled by the rate-controlling means, which in the present invention is a semipermeable membrane. The resulting delivery rate of the infusate to the needle assembly is thus dependant on the pressure created in the pressure-transmitting pouch. The invention described herein is intended to deliver low flow rates of infusate solution to the patient. For example, such a device might be sized to contain an infusate volume of from 1 to 20 ml, and to deliver this volume over a period of 2 hours to 7 days. Thus the invention is primarily intended for subcutaneous, as opposed to intravenous, delivery. The specific volume of infusate contained and total time for delivery would vary, however, depending on the choice of infusate, and would not necessarily be restricted to the quantities listed above. Therefore the infusion apparatus as herein described may be used for intravenous therapy where the infusate flow rate is consistent with the intended intravenous therapy.

In the embodiment described above, the first chamber contains a pouch that contains the infusate. Because the infusate pouch can be manufactured and filled separately from the rest of the device, it can be sterilized in a manner optimal for the drug and the pouch material. Thus, drugs that are sensitive to radiation, steam, or ethylene oxide sterilization can be filled into presterilized pouches by sterilizing filtration under aseptic conditions. The remainder of the pump components may be sterilized under more rigorous conditions or not sterilized at all. In one embodiment, the infusate pouch and its contents are stored separately from the rest of the pump assembly under conditions particularly suited for the drug, thus greatly increasing the shelf life of the completely assembled pump. Because only the infusate pouch material, the needle assembly, and the delivery tube come in contact with the infusate solution, only these components need be sterile.

The infusate pouch is constructed of flexible material that is relatively impermeable to both the infusate contained (on its inner surface) and, as insurance against leakage of the pressure-transmitting pouch, the osmotic medium and driving fluid (on its outer surface), during storage and use. The material used for manufacture of this pouch should be flexible so that pressure applied by the pressure-transmitting pouch to the infusate pouch causes delivery of the infusate. It is important that the materials used to fabricate the infusate pouch lack any substantial resistance to transmission of pressure developed in the pressure-transmitting pouch. That is, pressure developed in the pressure-transmitting pouch should be almost exactly transmitted to the infusate pouch, which will lead to flow of infusate out of the infusate pouch. Elastic materials can be used but are not preferred because most elastic materials are poor barriers to diffusion. In some cases, use of elastic materials could result in loss of the infusate solution or permit substances to diffuse into the infusate pouch (e.g. the driving fluid, if this fluid should leak out of the pressure-transmitting pouch). In addition, elastic materials are typically more vulnerable to attack and degradation caused by infusate solutions. Therefore, preferred materials for the infusate pouch are polyethylene, polypropylene, and copolymers thereof, Teflon ® (E. I. Du Pont de Nemours & Co., Wilmington, Del.), Barex ® (BP Chemicals International, Cleveland, Ohio), Tedlar ® (Du Pont), and polyfoil laminates of materials such as polyethylene (facing the drug solution) and aluminum foil outside the pouch.

The infusate contained in the infusate pouch may be in its final fluid form ready for delivery. In some instances, however, it may be preferable to store the infusate, e.g. a drug, in a lyophilized or otherwise desiccated form, in order to prolong the storage time of the drug. This would be of particular interest if the infusate pouch were to be stored with the rest of the pump assembly during the entire shelf life of the device. Therefore, in an alternate embodiment, the infusate pouch will be segmented into two compartments. One compartment will contain a lyophilized form of the infusate, and the other compartment will contain a pharmaceutically acceptable liquid solvent. In this embodiment, a seal between the two compartments would be broken by the user, or by a pharmacist or the like, before or during activation of the pump for use. To protect the infusate from degradation by diffusion of foreign substances into the drug-containing portion of the pouch during storage, and in particular the solvent, the seal must be made of impermeable materials. Preferred materials include metallized foil, metallized plastic film, and the like. This embodiment allows for storage of the infusate for long periods of time while insuring that the sterility of the pouch environment is not violated. In an alternate embodiment, the infusate pouch will contain a lyophilized form of the infusate, and the user or pharmacist will add a liquid solvent in an aseptic manner to the pouch either before or during activation of the pump.

As previously discussed, the pressure-transmitting pouch is in pressure-transmitting relationship with the infusate delivery pouch and contains the driving fluid as it is created in the pressure-transmitting pouch. The pressure-transmitting pouch, and in particular the area that is in pressure-transmitting relationship with the infusate delivery pouch, is made of flexible and preferably elastic materials so that it can exert pressure on the infusate pouch as driving fluid fills the pressure-transmitting pouch. These materials of construction should have an extended life and should be impermeable to the osmotic medium and the driving fluid, so that diffusion through the elastic walls will not contaminate the infusate during the delivery lifetime of the device. Preferred elastic materials include conventional rubbers, ethylene-propylene, butadiene-styrene, neoprene, and the like. The pressure-transmitting pouch contains the driving fluid as it is created by the pressure-generating means. The pressure-transmitting pouch also contains the osmotic medium prior to activation of the device. Preferred osmotic media are solid tablets or powders of salts, such as sodium chloride, magnesium sulfate, and sodium sulfate, salt solutions, such as sodium chloride solution; and water soluble organic liquids such as polyethylene glycol can also be used. Some sugars can also be used: dextrose, lactose, and fructose, for example, are all good candidates. The permeability of water across the semipermeable membrane is proportional to the osmotic pressure difference across the membrane, as described in Baker, R. W., *Controlled Release of Biologically Active Agents*; John Wiley & Sons: New York, 1987, p. 156. Typical salts that might be used, and their osmotic pressures, are listed in Table 1.

infusate pouch. This means that even if one film should have a failure that would allow leakage of a confined material, the driving fluid will not contaminate the infusate solution, although the pump may continue to deliver fluid out of the infusate pouch. Only in the very unlikely event of leaks or defects being found in both films would contamination occur. This is a considerable advantage over other designs for this type of device, in applications where patient safety is a critical issue. A second problem avoided by this design is the need to make the housing for the infusate pouch and the pressure-transmitting pouch fluid-tight. It should be noted that devices that do not have a separate pressure-transmitting pouch containing the driving fluid, for example the system described in U.S. Pat. No. 4,596,575, must be made absolutely leak-tight in order to function effectively. This type of construction is difficult to execute in an inexpensive, mass-produced unit, and leakage of the infusate or the driving fluid in this type of device on prolonged storage is a serious problem. By containing the driving fluid in a pouch, this problem is avoided. In the device described in this invention, it is desirable, however, to have relatively few air pockets in the spaces in the housing outside the pressure-transmitting pouch and the infusate pouch, or in the pressure-transmitting pouch itself. Although it is essential that the infusate pouch and the pressure-transmitting pouch are restrained in pressure-transmitting relationship, which can most commonly be obtained by enclosing the pouches in a common housing, one of ordinary skill in the art can design alternative arrangements where the pouches are contained in separate housings and are attached in such a manner to achieve substantially the same results. The various components of this invention, i.e., power source, infusate pouch, pressure-transmitting pouch, activating means, rate-controlling means, may all be located within the same housing or in separate housing as convenience dictates, but are intended to be included within the scope of this invention provided that these components have the interrelationships as described herein.

TABLE 1

| Salt | Vapor Pressure of Saturated Solution @ 20° C. in (% humidity) | Osmotic Pressure @ 20° C. in atm | Solubility in g / 100 g H₂O |
|---|---|---|---|
| NaCl | — | ~378.2 @ 25° C. | 36.5 |
| Pb(NO₃)₂ | 98 | 27 | 58.9 |
| KCl | — | ~216.7 @ 25° C. | 34 |
| Na₂HPO₄.12H₂O | 95 | 68.4 | 4.4 |
| NH₄H₂PO₄ | 93 | 96.8 | 128.4 |
| ZnSO₄.7H₂O | 90 | 140.6 | 57.7 |
| K₂CrO₄ | 88 | 170.6 | 64.6 |
| KHSO₄ | 86 | 207.2 | 57.4 |
| KBr | 84 | 232.6 | 68.3 |
| (NH₄)₂SO₄ | 81 | 281.1 | 74.1 |
| NH₄Cl | 79 | 314.5 | 35.7 |
| Na₂C₂H₃O₂.3H₂O | 76 | 366.1 | 50.6 |
| NaClO₃ | 75 | 383.8 | 106.8 |
| NaNO₂ | 66 | 554.4 | 84.4 |
| NaBr.2H₂O | 58 | 726.8 | 94.5 |
| Mg(NO₃)₂.6H₂O | 56 | 773.6 | 72.8 |
| Na₂Cr₂O₇.2H₂O | 52 | 872.4 | 176.8 |
| Zn(NO₃)₂.6H₂O | 42 | 1157.4 | 118.3 |
| CaCl₂.6H₂O | 31 | 1562.6 | 85.6 |
| KC₂H₃O₂ | 20 | 2147.3 | 219.2 |
| LiCl.H₂O | 15 | 2531.1 | 84.8 |

The use of an expanding pouch to transmit pressure to the infusate pouch has a number of advantages over the prior art. First, the driving fluid is separated from the infusate by two impermeable films, i.e. the walls of the pressure-transmitting pouch and the walls of the The power source is the third major component of the pump assembly. As previously described, the power source consists of a pressure-generating means, an activation means, and a rate-controlling means. The pressure-generating means causes the delivery of the driving fluid to the pressure-transmitting pouch. In the present invention, the pressure-generating means is the expansion of volume of the pressure-transmitting pouch caused by permeation of a fluid (the permeant) through a semipermeable membrane into a chamber that contains the osmotic medium. In a preferred embodiment, the permeant is water or another osmotically weak solution.

The activation means initiates the delivery of the driving fluid to the pressure transmitting pouch. Thus, the activation means allows for energizing of the pump at the user's discretion. For a Rose-Nelson pump design, the preferred activation means is rupturing of a seal that separates the permeant from the osmagent (osmotic medium). Rupturing of the seal starts the osmotic process that makes it possible for the permeant to enter the pressure-transmitting pouch, and thus begins creation of the driving fluid.

The rate-controlling means controls the flow of driving fluid into the pressure-transmitting pouch. It is an advantage of the present invention that the rate-controlling means is inherent in the design, because it is difficult to control the low flow rates using conventional valve technology. It is another advantage of the present invention that the fluid that is directly controlled is not the infusate, due to attendant problems with maintaining sterility of the rate-controlling means, and the need to avoid shear effects on the infusate. In the present invention, the rate-controlling means is a membrane that is permeable to the permeant and impermeable to the osmagent. When the pump is in use, the permeant travels through the semipermeable membrane, and the rate of pumping of fluid to the pressure transmitting pouch is thus controlled by the permeation properties of this membrane such as thickness, exposed area, permeation constant, etc. The preparation of the osmotic pumping device described in this disclosure requires a membrane with very high water permeability, due to the need to generate osmotic pressure rapidly. Cellulose acetate is an especially preferred membrane material for this application because its water permeability is high and can be adjusted easily by varying the degree of acetylation of the polymer. As discussed in U.S. Pat. Nos. 4,077,407 and 4,838,862, each incorporated herein by reference in its entirety, the permeability of cellulose acetate membranes can be increased further by adding plasticizers to the polymer to increase the water diffusion coefficient, or by adding hydrophilic flux enhancers, which increase the water sorption of the membrane. Some hydrophilic plasticizers serve both purposes. The effect of the hydrophilic plasticizer polyethylene glycol on the osmotic water permeability of cellulose acetate membranes is substantial; the water permeability is increased more than four-fold by the addition of polyethylene glycol. Addition of the hydrophilic polymer hydroxybutyl methyl cellulose to the cellulose acetate membrane has a similar effect. Thus certain membrane materials can be tailored so that their permeability characteristics are made suitable for the particular application at hand, i.e. so that, in the device created, the infusate is delivered to the patient at the desired flow rate.

The infusate leaves the infusate pouch through a dispensing nozzle and a connecting means. In one embodiment, the end of the connecting means may be adapted for use with a skin-piercing needle or a standard commercial subcutaneous drug delivery set, for example, the Sub-Q-Set® (Travenol Laboratories, Deerfield, Ill.). Alternately the tube may be inserted into one of the normal body orifices or into a previously established indwelling catheter.

The device assembly can be attached to the body of the wearer by means of a biocompatible adhesive coating on the base of the assembly, or by adhesive strips or overlays, and does not mandate the use of straps, belts, or other carrying garments. The device may be attached anywhere on the body that is convenient, either immediately adjacent to the delivery site, or at a point distant from that site.

The choice of components used in the various foregoing general descriptions and the following detailed descriptions are exemplary and explanatory, but are not restrictive of the invention.

Because the devices described in the present invention are small and simple, they are particularly suitable for delivering small infusate volumes to the patient. For example, such a device might be sized to contain an infusate volume of from 1 to 20 ml, and to deliver this volume over a period of from 2 hours to 7 days. (The specific volume of infusate contained and total time for delivery would vary depending on the choice of infusate, and would not necessarily be restricted to these quantities.) Thus, the invention enables therapy involving highly potent substances, such as peptide drugs of various kinds, heparin and insulin, analgesics and anesthetics, corticosteroids, immunosuppressants, antineoplastics, antibacterials, and antidotes to chemical or biological poisons and the like, to be administered without subjecting the patient to repeated injections or requiring immobilization of the patient with continuous intravenous therapy.

A number of drug are particularly suited for delivery via the instant infusion device including but not limited to heparin, insulin, chemotherapeutic agents such as fluorouracil, cisplatin, antibiotics such as adriamycin, oncovin, bleomycin, vancomycin, tobramycin, antinauseants such as haldol, benadryl, antivirals such as gancyclovir, and analgesics such as morphine, codeine, fentanyl, ketorolac, dilaudid and the like.

The infusion device can be assembled with its components and stored for periods of months or years without deterioration. In a particularly preferred embodiment, the infusate is stored in the infusate pouch separately from the rest of the pump assembly. When ready for use, the patient or pharmacist or the like can insert the infusate pouch into the device. The device can be activated on demand by the user or therapist.

DETAILED DESCRIPTION OF THy INVENTION

Definition of terms

The term "drug" as used herein denotes any medication composition (as defined, below); in any way affecting any human or animal entity; substance to be assimilated by any human being or animal for its nourishment or for regulating its growth; substance exhibiting any of the above activities to be directly applied to the habitat, surroundings or environment of any of the above organisms; and substance having any other effect on any other environment, especially any aqueous environment.

Therefore, suitable drugs for use with the dispenser of this invention include, without limitation, those that are generally capable of:

1. Preventing, alleviating, treating, or curing abnormal or pathological conditions of the living body by such means as destroying a parasitic organism or limiting the effect of the disease or abnormality by chemically altering the physiology of the host or parasite;

2. Maintaining, increasing, decreasing, limiting or destroying a physiologic body function, e.g. vitamin compositions, sex sterilants, fertility inhibitors, fertility promoters, growth promoters, and the like;

3. Diagnosing a physiological condition or state;

4. Controlling or protecting an environment or living body by attracting, disabling, inhibiting, killing, modifying, repelling, or retarding an animal or microorganism, such as food and nonfood baits, attractants and lures, biocides, pesticides, algicides, parasiticides, rodenticides, insecticides, fungicides, and the like;

5. Preserving, disinfecting, or sterilizing; and

6. Controlling or affecting generically an environment, as by introducing a catalyst or metering a reactant into a reacting chemical system, or by effecting any chemical process therein, such as fermentation, including propagation and/or attenuation of a microorganism.

infusate is herein defined as a liquid drug or a solution, gel or suspension of drug that is delivered from the infusate pouch. Driving fluid is herein defined as the liquid contained in the pressure-transmitting pouch that is used to increase the size of the pressure transmitting pouch, and will consist of the solution that results when the permeant passes through the semipermeable membrane and contacts the osmotic medium (osmagent).

Detailed description of the figures

Figure 2:
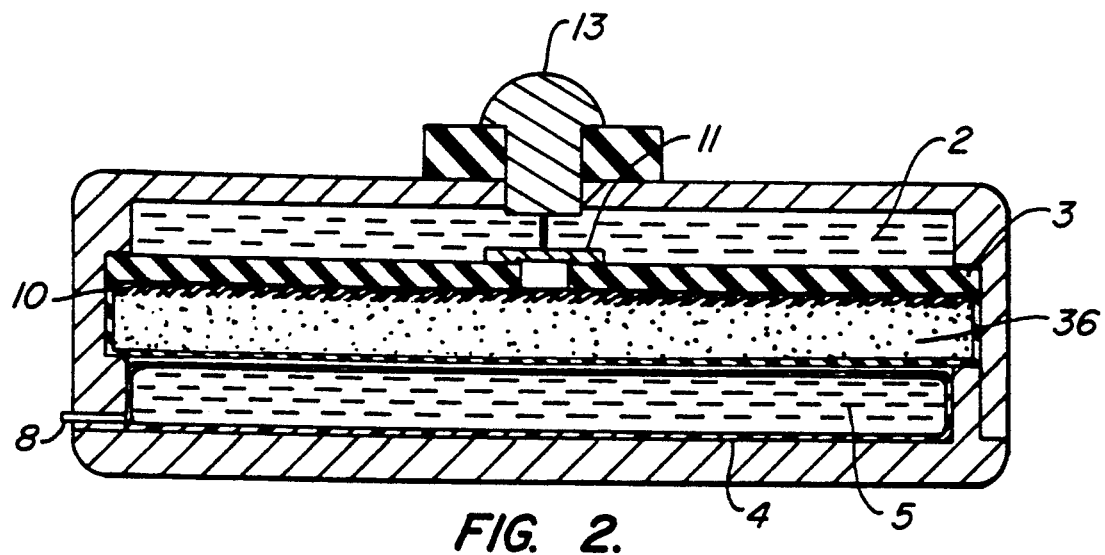
FIG. 2 is a diagram illustrating the operating principle of the invention.
Figure 3A:
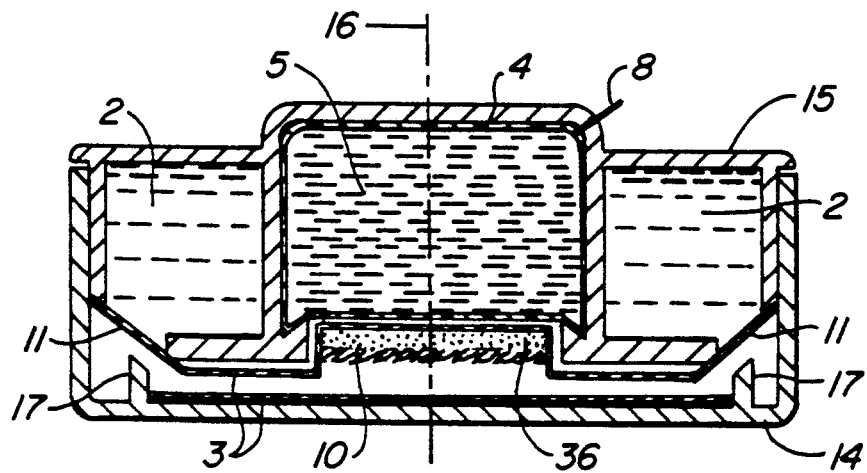
FIG. 3A is a partial cross-section illustrating the operating principle of the invention.
Figure 3B:
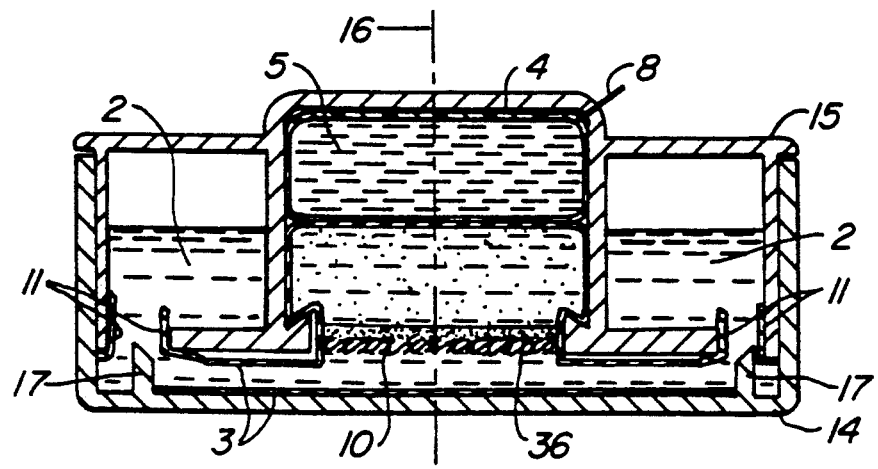
FIG. 3B is a partial cross-section illustrating the operating principle of the invention.

Referring now to the drawings, not drawn to scale, FIGS. 1, 2, and 3 illustrate devices based on the Rose-Nelson osmotic pump. A general plan of the invention is shown in FIG. 1. The pressure-generating means is an osmotic pump of the Rose-Nelson type. The pressure-generating means causes delivery of the driving fluid 12 to the pressure-transmitting pouch 3. The permeant 2 for this pump is normally water, although any liquid capable of generating an osmotic pressure in conjunction with the osmagent could be used. Before activation of the device, the permeant 2 is contained in a chamber 1 separated from contact with the semipermeable membrane 10 and the pressure-transmitting pouch 3 by a seal 11 that is ruptured immediately prior to use by the patient. In a preferred embodiment, seal 11 is made from metal foil, metallized film, or the like. In another embodiment, the device may have release pins that, when broken, rupture seal 11 and allow the power chamber to be moved within the device so that permeant 2 comes in contact with semipermeable membrane 10. Seal 11 is ruptured immediately prior to use by an activation means that rips or breaks the seal. In the device shown in FIG. 1, seal 11 is attached to plunger 13. Thus when plunger 13 is rotated, the seal is ripped and permeant 2 contacts and wets membrane 10.

A number of different activating means are disclosed in co-owned U.S. Pat. Nos. 4,838,862 and 4,898,582, herein incorporated by reference, including valves and the like, are encompassed in the scope of this invention.

Figure 6:
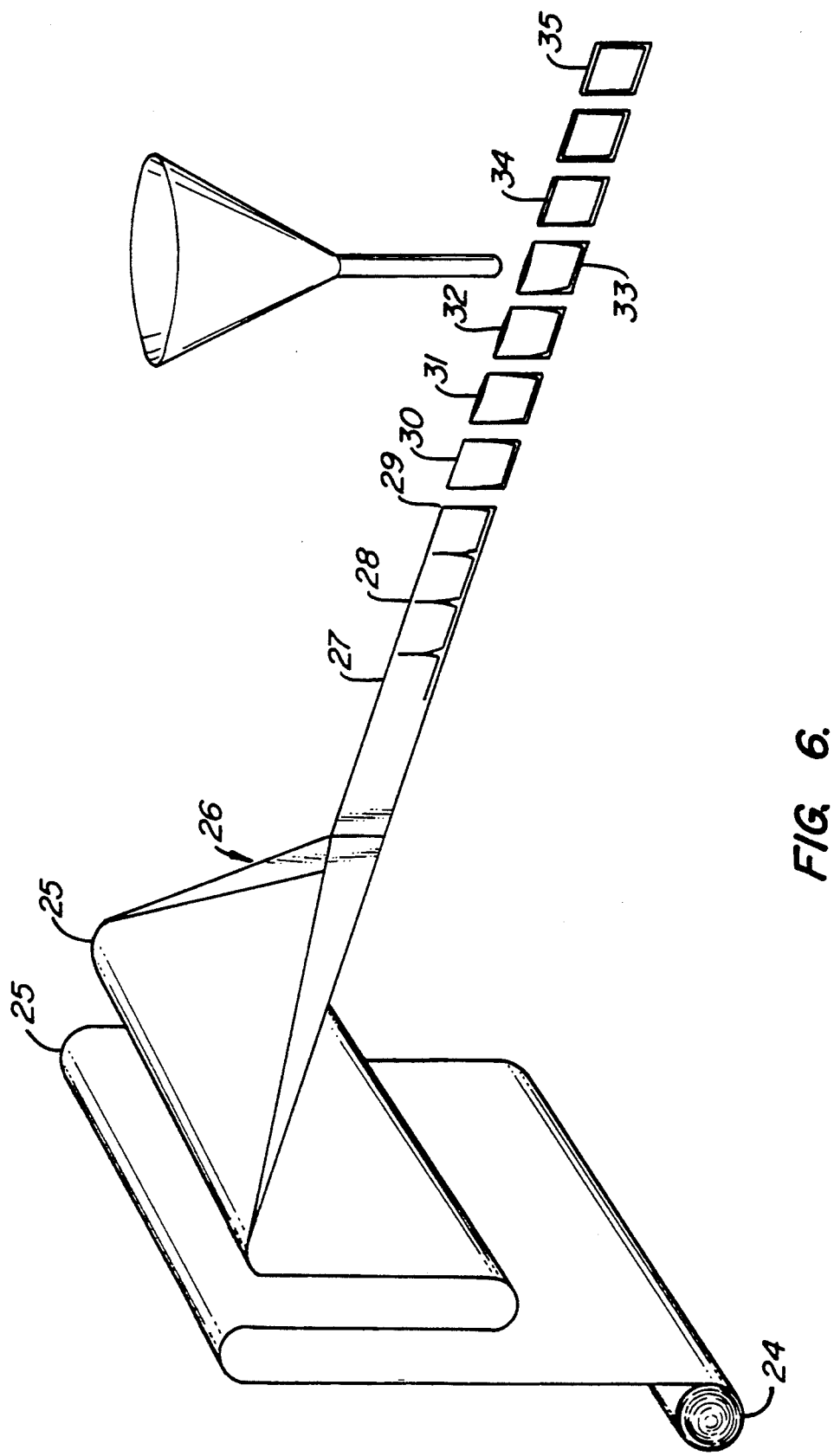
FIG. 6 is a diagram of a packaging process for creating, filling, and sealing the infusate pouch aseptically and separately from the pump assembly.

The semipermeable membrane 10 is shown in FIG. 1 as being contained within the first chamber, but it can alternately be contained in chamber 7. The seal 11 is made from metal foil, metallized film or the like. When the device is in use, the permeant travels through the semipermeable membrane 10 into the pressure-transmitting pouch 3, which contains an osmagent that may be a salt tablet or osmotic solution 36. The delivery rate of the pump depends on the area, thickness, and permeability of the semipermeable membrane. Hence the choice of a suitable membrane material is essential to good performance of the pump. A preferred choice is a membrane made from one of the cellulose esters or ethers, such as cellulose acetate or cellulose butyrate. Cellulose acetate has a long record of use in membrane applications and can be formed easily into thin films of reproducible thickness with standard solution casting techniques, making it a particularly preferred choice. Other choices for membrane material include polyamides; nylon 6; nylon 6-6; aromatic polyamides, for example, the aromatic polyamide sold under the name Nomex ® (Du Pont); cellulose acetate butyrate; ethylcellulose; cellulose nitrate; blends of cellulose acetates of various degrees of acetylation; or various types of cellulosic esters and ethers. Many other semipermeable membranes are known and discussed, for example, in *Reverse Osmosis and Synthetic Membranes: Theory—Technology—Engineering* (Sourirajan, S., Ed., National Research Council Canada, Division of Chemistry, National Research Council of Canada: Ottawa, Canada, 1977, NRCC No. 15627.) The osmotic pressure developed by the diffusion of permeant 2 through semipermeable membrane 10 into pressure-transmitting pouch 3 is exerted on infusate pouch 4. It is a particular advantage of this system that the rate controlling means is inherent in the design, because it is difficult to control the low flow rates (up to 10–20 ml per day) using conventional valve technology. A wide range of appropriate, solutes and membrane materials for use in osmotic pumps is disclosed in U.S. Pat. No. 4,034,756, which is incorporated herein by reference. Preferred salts are sodium chloride, potassium chloride, magnesium sulfate, and sodium sulfate. Osmosis is in general a rather slow constant process, and thus in general this type of device is preferred when infusion of rather small volumes of infusate at low flow rates is required. For example, such a device might be sized to contain an infusate volume of from 1 to 20 ml, and to deliver this volume over a period of 2 hours to 7 days. The specific volume of infusate contained and total time for delivery would vary depending on the choice of infusate, and would not necessarily be restricted to these quantities. Creation of driving fluid expands the pressure transmitting pouch, therefore, the pressure-transmitting pouch must be made, at least in part, of a flexible or elastic material, particularly the surface of the pressure-transmitting pouch facing the infusate containing infusate pouch 4. Elastic materials are especially preferred, because the surface of the pressure-transmitting pouch 3 that is in pressure-transmitting relationship with the infusate pouch functions best when it is expandable. Preferred elastic materials include conventional rubbers, ethylene-propylene, butadiene-styrene, neoprene, and the like. The pressure-transmitting pouch 3 may be made of a single material or can be made by gluing or heat sealing two or more dissimilar materials together to form the pouch. The infusate pouch 4 is made of flexible materials, but normally is not made of elastic materials because most elastic materials are vulnerable to diffusion of the infusate out of the infusate pouch, or of diffusion of the driving fluid into the infusate pouch, if this fluid should leak out of the pressure-transmitting pouch 3. In addition, elastic materials would typically be more vulnerable to attack and degradation caused by the infusate solution. Therefore, preferred materials for the infusate pouch 4 are inert polymers such as polyethylene, polypropylene, and copolymers thereof, Teflon ® (E. I. Du Pont de Nemours & Co., Wilmington, Del.), Barex ® (BP Chemicals International, Cleveland, Ohio), Tedlar ® (Du Pont), and polyfoil laminates of materials such as polyethylene (facing the infusate solution) and aluminum foil outside the infusate pouch. It is a major advantage of this invention that the infusate solution contacts inert, stable, sterilizable, nonleaching materials, and is essentially impervious to contaminants from the outside environment. In one embodiment, the infusate pouch 4 is formed and filled with infusate solution in a single operation using a heat-sealing form-fill-and-seal technology widely used in industry today. This technology is used, for example, to form small polyfoil bags containing foods such as ketchup and mustard or transdermal drug delivery systems. This technology is amenable to very high production rates at low cost and can be maintained under aseptic conditions. FIG. 6 illustrates an embodiment of this type of packaging system. The pressure-transmitting pouch 3, infusate pouch 4, and semipermeable membrane 10 are contained in a housing 7 that is restraining and should be nonirritating to the skin and nonreactive and impervious to the salts, solutions, agents and the like, contained therein. In one embodiment, this housing also encloses the power source, i.e. chamber 1, permeant 2, activation means 13, and seal 11, so as to protect them from the environment. In another embodiment, only the pressure-transmitting pouch, infusate pouch, and semipermeable membrane are contained in the housing. Preferred materials for housing 7 are stainless steel, aluminum, polyolefins, polycarbonate and the like. An infusate connecting means 8 is attached to the dispensing nozzle 6 of the infusate pouch and by means of the needle assembly 9 to the patient. The needle assembly may be a skin piercing needle or a standard commercial subcutaneous delivery set, for example, the Sub-Q-Set ® (Travenol Laboratories, Deerfield, Ill.). Alternately the infusate delivery tube may be inserted into one of the normal body orifices.

An alternative configuration of the activation mechanism is illustrated in FIG. 2. In this device, the seal 11 is broken when plunger 13 is depressed. This action brings permeant 2 in contact with membrane 10. Yet another alternative configuration of the activation mechanism is shown in FIG. 3. This device is constructed in two sections, 14 and 15, that can be rotated around control axis 16. Before activation, seal 11 is above the level of pins 17 and prevented from contact with pins 17. Activation occurs when the top section lowered so that is rotated so that the seal now comes in contact with the pin. Rotation of the top portion completes the activation step by further rupture and tearing of the seal. Before activation, the seal is above the level of the pins 17. When the top section is lowered and rotated, the portion of the seal that is in the same plane as the pins now comes in contact with the pins. The seal is then torn and broken. The breaking of seal 11 allows permeant 2 to come in contact with membrane 10.

Figure 4A:
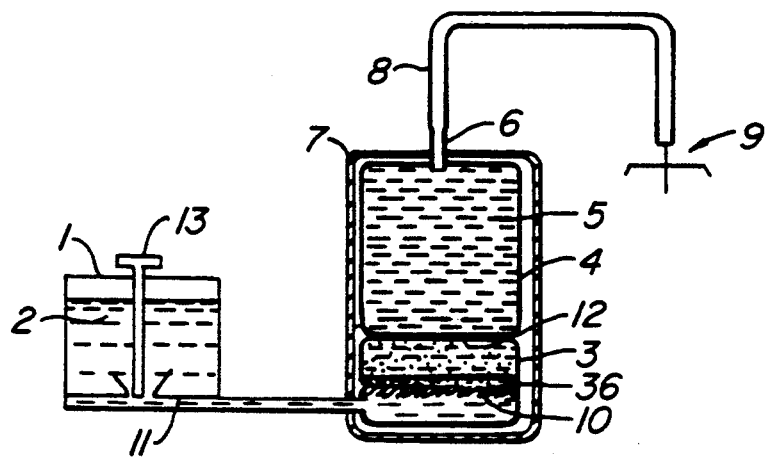
FIG. 4A is a diagram illustrating the operating principle of the invention.
Figure 4B:
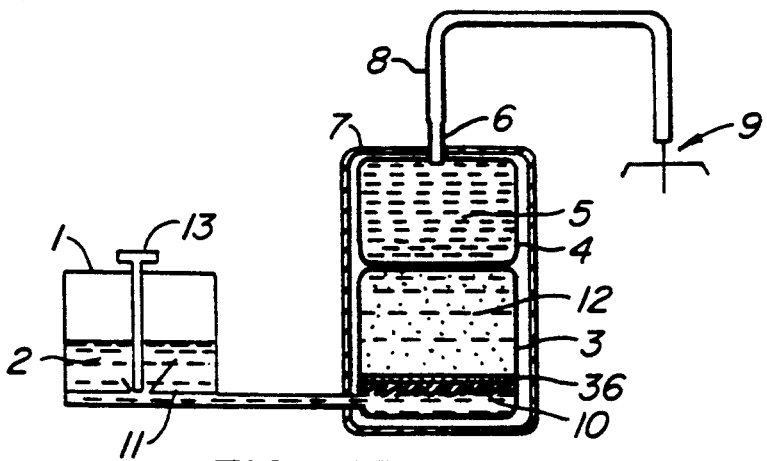
FIG. 4B is a partial cross-section illustrating the operating principle of the invention.
Figure 4C:
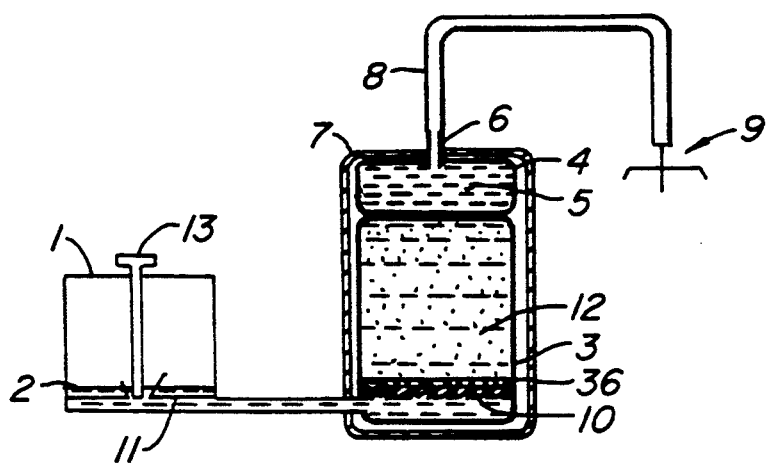
FIG. 4C is a partial cross-section illustrating the operating principle of the invention.

FIG. 4 illustrates the operation of the embodiment of the device described in FIG. 1. FIG. 4a illustrates activation of the device, where seal 11 is broken by the activation means, in this case plunger 13. The permeant 2 contacts semipermeable membrane 10 and begins to penetrate it. The entrance of permeant into the pressure-transmitting pouch 3 creates driving fluid and increases the volume of this pouch. Thus the pressure-transmitting pouch begins to exert pressure on infusate pouch 4. In FIG. 4b, permeant 2 continues to pass through semipermeable membrane 10 and into pressure-transmitting pouch 3, thereby creating more driving fluid. The pressure on infusate pouch 4 causes infusate 5 to be forced out of the pouch, through dispensing nozzle 6, delivery tube 8, and needle assembly 9, and into the patient. In FIG. 4c this process has continued to the point where most of permeant 2 has left chamber 1, and the pressure created by driving fluid 12 has forced most of infusate 5 out of the pouch. If there is more permeant than infusate in the system, the pumping activity will continue until either the supply of infusate or driving fluid is exhausted. A problem with having a greater supply of permeant than infusate, however, is that once the infusate pouch is empty the pump will continue working, and may spring leaks if the pressures that build up cannot be contained by the housing. If the osmagent is a solid salt, the pumping rate will be constant as long as there is undissolved salt available, i.e. as long as the driving fluid is saturated. If all of the solid salt is dissolved, or if an osmotic solution is used as the osmagent, the pumping rate will decline as the concentration of the driving fluid decreases, but the pump will still continue working. One solution to the problem is to load the pump with more infusate than permeant. When all of the permeant has crossed the membrane, the pumping then stops.

In another embodiment of the invention, shown in FIG. 5, infusate pouch 22 is divided into two compartments for the purpose of storing the drug 18 in lyophilized or otherwise desiccated form, so as to prolong the shelf life of the device. In this embodiment, compartment 21 of infusate pouch 22 contains lyophilized drug and is separated from the solvent compartment 23 of pouch 22 by rupturable seal 20. This seal 20 must be impermeable to both the lyophilized drug 18 and the liquid solvent 19; therefore, a preferred material for this seal is a metallized foil, metallized plastic film, or the like. Seal 20 is ruptured by the user immediately before or during activation of the device, to allow mixing of lyophilized drug 18 and liquid solvent 19 before delivery of the infusate to the patient.

FIG. 6 is a diagram of a packaging process for creating, filling, and sealing the infusate pouch aseptically and separately from the pump assembly. It presents an overview of the process that illustrates how a roll of packaging material is formed and filled, how seals are created in the material, and how the packages are separated into individual pouches. Web roll 24 holds a rolled supply of the pouch material, ready to be unrolled into tensioning unit 25 and plow assembly 26, which folds the strip of material in half. At station 27 the strip is sealed at the fold to create the bottom fold, and at station 28 the side sealing is accomplished at desired intervals. At station 29 the pouches are cut into individual units, and at stations 30 and 31 the pouches are positioned and opened to receive the infusate. At station 32 the pouches are formed to prepare them for filling, and at station 33 the pouches are filled with infusate. In one embodiment, a simple funnel system is used to deliver the infusate to the individual pouches. At station 34 dispensing nozzles are attached and the pouches receive their top seals, and at station 35 the completed pouches are ready to be removed from the system and delivered to the next packaging station.

The invention has been described and illustrated with reference to certain preferred embodiments thereof, but those skilled in the art will appreciate that various modifications, changes, omissions, and substitutions can be made without departing from the spirit of the invention. For example, one skilled in the art might construct the infusion pouch with a fill port so that it may be filled by the user, pharmacist, or the like, just prior to activation. It is intended, therefore, that the invention be limited only by the scope of the following claims.

We claim:

1. A portable infusion device assembly comprising:
   a. a first pouch containing infusate and fitted with a dispensing nozzle;
   b. a second pouch in pressure-transmitting relationship to the aforesaid first pouch;
   c. an integral power source comprising:
      a pressure-generating means for generating pressure in aforesaid second pouch, comprised of an osmagent and a liquid permeant, wherein a driving fluid is produced when permeant contacts osmagent;
      an activating means for initiating the action of the aforesaid power generating means;
      a rate-controlling means for regulating the volume change of the aforesaid first pouch, comprising a semipermeable membrane;
   d. a fluid-transport means in liquid transmitting relationship between the aforesaid power chamber and the aforesaid delivery chamber, and,
   e. a connecting means for attaching the aforesaid dispensing nozzle to the object of treatment; and,
   f. a housing containing the aforesaid first and second pouches and in restraining relationship to the aforesaid first and second pouch.

2. A portable infusion device assembly comprising:
   a. a first pouch containing infusate and fitted with a dispensing nozzle;
   b. a second pouch in pressure-transmitting relationship to the aforesaid first pouch;
   c. an integral power source comprising:
      a pressure-generating means for generating pressure in aforesaid second pouch, comprised of an osmagent and a liquid permeant, wherein a driving fluid is produced when permeant contacts osmagent;
      an activating means for initiating the action of the aforesaid power generating means;
      a rate controlling means for regulating the volume change of the aforesaid first pouch, comprising a semipermeable membrane;
   d. a fluid-transport means in liquid transmitting relationship between the aforesaid power chamber and the aforesaid delivery chamber, and,
   e. a connecting means for attaching the aforesaid dispensing nozzle to the object of treatment; and,
   f. a housing containing the aforesaid first pouch, second pouch, and power source, and in restraining relationship with the aforesaid first and second pouches.

3. The device according to claim 1 where the inner space of the first infusate pouch is comprised of:
   a. drug in dry form;
   b. pharmaceutically acceptable solvent for said drug; and,
   c. a breakable seal in separating relationship to said drug and solvent.

4. The device according to claim 2 where the inner space of the first infusate pouch is comprised of:
   a. drug in dry form;
   b. pharmaceutically acceptable solvent for said drug; and,
   c. a breakable seal in separating relationship to said drug and solvent.

5. A method for infusing a patient, comprising connection of said patient to a portable infusion device, said device comprising:
   a. a first pouch containing infusate and a dispensing nozzle;
   b. a second pouch in pressure-transmitting relationship to the aforesaid first pouch;
   c. an integral power source comprising:
      a pressure-generating means for generating pressure in aforesaid second pouch, comprised of an osmagent and a liquid permeant, wherein a driving fluid is produced when permeant contacts osmagent;
      an activating means for initiating the action of the aforesaid power generating means;
      a rate-controlling means for regulating the volume change of the aforesaid first pouch, comprising a semipermeable membrane;
   d. a connecting means for attaching the aforesaid dispensing nozzle to the object of treatment;
   e. a housing containing the aforesaid first and second pouches and in restraining relationship to the aforesaid first and second pouches; and,
   f. activating said device.

6. A method for infusing a patient, comprising connection of said patient to a portable infusion device, said device comprising:
   a. a first pouch containing infusate and a dispensing nozzle;
   b. a second pouch in pressure-transmitting relationship to the aforesaid first pouch;
   c. an integral power source comprising:
      a pressure-generating means for generating pressure in aforesaid second pouch, comprised of an osmagent and a liquid permeant;
      wherein a driving fluid is produced when permeant contacts osmagent;
      an activating means for initiating the action of the aforesaid power generating means;
      a rate controlling means for regulating the volume change of the aforesaid first pouch, comprising a semipermeable membrane;
   d. a connecting means for attaching the aforesaid dispensing nozzle to the object of treatment;
   e. a housing containing the aforesaid first pouch, second pouch, and power source, and in restraining relationship with the aforesaid first and second pouches; and,
   f. activating said device.

7. The device of claim 1, where said pouch for containment of the infusate is loaded with infusate separately from the rest of the device assembly, and can then be inserted into said assembly.

8. The device of claim 2, where said pouch for containment of the infusate can be loaded with infusate separately from the rest of the device assembly, and is then be inserted into said assembly.

9. The device of claim 1, where said activation means is comprised of a means of breaking a barrier separating the permeant from contact with the semipermeable membrane that is the rate-controlling means.

10. The device of claim 2, where said activation means is comprised of a means of breaking a barrier separating the permeant from contact with the semipermeable membrane that is the rate-controlling means.

11. The device of claim 9, where:
a. said activation means is a plunger or other means of breaking said barrier; and,
b. said barrier is a seal separating the permeant from contact with the semipermeable membrane.

12. The device of claim 10, where:
a. said activation means is a plunger or other means of breaking said barrier; and,
b. said barrier is a seal separating the permeant from contact with the semipermeable membrane.

13. The device according to claim 1 where the drug contained in the infusate pouch is heparin.

14. The device according to claim 1 where the drug contained in the infusate pouch is insulin.

15. The device according to claim 2 where the drug contained in the infusate pouch is heparin.

16. The device according to claim 2 where the drug contained in the infusate pouch is insulin.

17. The device according to claim 1 where the drug contained in the infusate pouch is fluorouracil.

18. The device according to claim 2 where the drug contained in the infusate pouch is fluorouracil.

19. The device according to claim 1 where the drug contained in the infusate pouch is cisplatin.

20. The device according to claim 2 where the drug contained in the infusate pouch is cisplatin.

21. The device according to claim 1 where the drug contained in the infusate pouch is gancyclovir.

22. The device according to claim 2 where the drug contained in the infusate pouch is gancyclovir.

23. The device according to claim 1 where the drug contained in the infusate pouch is adriamycin.

24. The device according to claim 2 where the drug contained in the infusate pouch is adriamycin.

* * * * *